United States Patent [19]
Wakamatsu et al.

[11] Patent Number: 4,831,180
[45] Date of Patent: * May 16, 1989

[54] PROCESS FOR PRODUCING ALPHA-L-ASPARTYL-L-PHENYLALANINE METHYL ESTER HAVING AN IMPROVED SOLUBILITY

[75] Inventors: Hidetoshi Wakamatsu, Shin-nanyo; Shigeaki Irino, Yamaguchi; Tsuneo Harada; Akira Tokuda, both of Shin-nanyo; Hiyotaka Oyama, Hikari, all of Japan

[73] Assignee: Toyo Soda Manufacturing Company, Ltd., Yamaguchi, Japan

[*] Notice: The portion of the term of this patent subsequent to Mar. 7, 2006 has been disclaimed.

[21] Appl. No.: 84,090

[22] Filed: Aug. 11, 1987

[30] Foreign Application Priority Data

Aug. 12, 1986 [JP] Japan .................... 61-187757

[51] Int. Cl.$^4$ ............................ C07C 101/02
[52] U.S. Cl. .................................... 560/41
[58] Field of Search ............ 560/41; 530/801; 426/548; 34/10, 76, 31

[56] References Cited

U.S. PATENT DOCUMENTS 4,579,747  4/1986  Sugiyama et al. ............... 426/548

FOREIGN PATENT DOCUMENTS 57-42623    7/1982  Japan .
59-172444   6/1984  Japan .
59-95862    9/1984  Japan .
60-37949    3/1985  Japan .

OTHER PUBLICATIONS

Perry et al, *Chemical Engineers' Handbook*, 5th ed., McGraw-Hill, New York, pp. 20-4 to 20-16 (1973).
"Application Potential For Aspartame in Low Calorie and Dietetic Foods", In Low Calorie and Special Dietary Foods, pp. 59-114, CRC Press 1978 CRF 21, Food and Drugs Revised as of Apr. 1, 1981.

*Primary Examiner*—Bruce D. Gray
*Attorney, Agent, or Firm*—Nixon & Vanderhye

[57] ABSTRACT

A process for producing dry α-L-aspartyl-L-phenylalanine methyl ester having an improved solubility by drying wet crystals of α-L-aspartyl-L-phenylalanine methyl ester, characterized in that the wet crystals of α-L-aspartyl-L-phenylalanine methyl ester are granulated so that the specific surface area during the drying operation is at least 4 m$^2$/g, followed by drying.

5 Claims, No Drawings

PROCESS FOR PRODUCING ALPHA-L-ASPARTYL-L-PHENYLALANINE METHYL ESTER HAVING AN IMPROVED SOLUBILITY

The present invention relates to a process for producing α-L-aspartyl-L-phenylalanine methyl ester (hereinafter referred to as Aspartame) having an improved solubility.

Heretofore, various methods have been proposed to obtain Aspartame having an excellent solubility. For example, it has been proposed to granulate Aspartame together with an excipient having an excellent solubility, to form it into disintegrating tablets in combination with an excipient and a disintegrator, or to form it into effervescing tablets in combination with an effervescing agent and a neutralizing agent. Another method is known wherein a specific amount of water is added to Aspartame II type crystals, followed by mixing, granulating and drying (Japanese Unexamined Patent Publication No. 95862/1984). It is known that there are two types of Aspartame crystals, i.e. I and II type crystals (Japanese Unexamined Patent Publication Nos. 172444/1984 and 37949/1985). Aspartame II type crystals have a low hygroscopicity and an excellent storage stability, as compared with the I type crystals. Therefore, the process for producing Aspartame II type crystals have been extensively studied. However, no substantial studies have been made on Aspartame I type crystals.

Aspartame has poor dispersibility and solubility in water. In its application to food, Aspartame is likely to form agglomerates due to the poor dispersibility and solubility when dissolved, which make the operation of dissolving it in water difficult and time-consuming.

In conventional methods, it is necessary to dissolve Aspartame in water or to form it into a slurry once. Therefore, there are problems with respect to the operation, the process control and costs for energy. On the other hand, if other substances are mixed to Aspartame to improve the solubility, the presence of such substances may likely be a problem depending upon a particular use. Therefore, there is strong demand for highly pure Aspartame having an excellent solubility.

According to the studies by the present inventors, of the above-mentioned two types of Aspartame crystals, the I type crystals are far superior in the solubility to the II type crystals. A product obtained by drying wet Aspartame crystals by an industrial method, is usually a mixture of the I and II type crystals.

In particular, the ratio of Aspartame II type crystals is larger in the case where Aspartame is granulated, followed by drying. Wet Aspartame crystals are usually obtained in the form of crystals having a relatively small size, and when dried as they are, they will be powdery whereby it becomes difficult to handle them. Therefore, it is an important technique wherein wet Aspartame is granulated, followed by drying.

Therefore, even when Aspartame is dried after granulation, it is an important technical subject to develop an industrial process for the production of the I type crystals containing no or only a small amount of the II type crystals.

The present invention provides a process for producing dry α-L-aspartyl-L-phenylalanine methyl ester having an improved solubility by drying wet crystals of α-L-aspartyl-L-phenylalanine methyl ester, characterized in that the wet crystals of α-L-aspartyl-L-phenylalanine methyl ester are granulated so that the specific surface area during the drying operation is at least 4 $m^2/g$, followed by drying.

In the present invention, the wet crystals of Aspartame used as the starting material to obtain dry Aspartame having an improved solubility, may be prepared by any crystallization and separation methods. Thus, there is no restriction as to the method of producing wet Aspartame crystals. Namely, wet Aspartame crystals used in the present invention may be prepared by an appropriate crystallization method, followed by a solid-liquid separation.

When wet Aspartame crystals are granulated and then dried, the ratio of Aspartame II type crystals in the resulting Aspartame granules usually significantly increases.

The present inventors have found that formation of Aspartame II type crystals by drying can be suppressed to a low level, if wet Aspartame crystals are granulated to have a specific surface area of at least 4 $m^2/g$.

Aspartame granules having a specific surface area of at least 4 $m^2/g$ are obtainable by reducing the degrees of the kneading and the compression of wet Aspartame crystals in the granulating step. Wet Aspartame crystals prepared may be treated by any type of a granulator such as an extrusion granulation type, a compression granulation type.

According to the present invention, there is no particular restriction as to the temperature and the drier. However, Aspartame is not stable at a high temperature, and when it is dried at a high temperature, a part of Aspartame is readily converted to a diketopiperadine derivative. The diketopiperadine derivative is non-toxic and safe, but it lacks in sweetness, thus leading to a loss of overall sweetness. Whereas, the higher the drying temperature, the higher the conversion of Aspartame crystals to Aspartame II type crystals. Therefore, Aspartame is dried preferably at a temperature of lower than 80° C.

Now, the present invention will be described in further detail with reference to Examples. However, it should be understood that the present invention is by no means restricted to these specific Examples.

In the Examples, the ratio of I type crystals (i.e. the ratio of the I type crystals to the total amount of the I and II type crystals) was determined as follows: Standard samples of the I and II type crystals were mixed at various ratios, and a calibration curve was prepared based on strength ratios of the respective X-ray diffraction specific peaks, where the I and II type crystals exhibit the X-ray diffraction specific peaks at angles ($2\theta$) of diffraction of 4.4° and 5.0°, respectively. Then, the ratio of the I type crystals was determined by comparing the strength ratio of each sample with the calibration curve.

In the Examples, the solubility of Aspartame crystals was determined by measuring the duration till 1 g of Aspartame crystals which was added to 500 ml of distilled water at 20° C., followed by stirring (by a magnetic stirrer at 200 r.p.m.), was completely dissolved as visually observed.

EXAMPLE 1

Wet Aspartame crystals (30 kg) obtained by a solid-liquid separation by means of a centrifugal separator, was extruded through a screen having a mesh size of 2 mm, and granulated to have a specific surface area of at least 4 m²/g, and then dried in a fluidized-bed drier by means of a hot air stream of 70° C. for 2 hours to obtain 12.4 kg of a dry Aspartame product having a water content of 2.0 % by weight.

On the other hand, for the purpose of comparison, the same granulated wet crystals (30 kg) were dried in the fluidized-bed drier by means of a hot air stream for 1 hour to obtain 11.8 kg of a dry Aspartame product having a water content of 1.7% by weight.

TABLE 1

| Number of Example or Comparative Example | Specific surface area (m²/g) | Final water content (%) | Solubility (min) | Ratio of I type crystals (%) |
| --- | --- | --- | --- | --- |
| Example 1 | 5.4 | 2.0 | 5-6 | 94 |
| Comparative Example 1 | 3.7 | 1.7 | 11-12 | 55 |

EXAMPLES 2 TO 5

Wet Aspartame crystals prepared in the same manner as in Example 1, were extruded through a screen having a mesh size of 2 mm in diameter, and granulated to have a specific surface area of at least 4 m²/g. Granulated wet Aspartame crystals (30 kg) having various specific surface areas were dried in the fluidized-bed drier by means of a hot air stream of 70° C. to obtain a dry Aspartame product.

The results are shown in Table 2.

TABLE 2

| Number of Examples | Specific surface area (m²/g) | Final water content (%) | Solubility (min) | Ratio of I type crystals (%) |
| --- | --- | --- | --- | --- |
| Example 2 | 4.35 | 1.8 | 6-7 | 87 |
| Example 3 | 5.05 | 2.3 | 5-6 | 90 |
| Example 4 | 5.65 | 2.5 | 5-6 | 93 |
| Example 5 | 7.16 | 2.0 | 4-5 | 98 |

As is apparent from the foregoing description, according to the present invention, it is possible to obtain dry Aspartame having an excellent solubility without disadvantages with respect to the process control and costs for energy, or without necessity of mixing it with other substances.

The dry Aspartame product having an improved solubility of the present invention is widely useful as a sweetener for soft drinks, a table sweetener or a sweetener for other foods.

We claim:

1. A process for producing dry granules of α-L-aspartyl-phenylalanine methyl ester having an improved solubility, said process comprising the steps of:
   granulating wet crystals of α-L-aspartyl-phenylalanine methyl ester to produce wet crystals of α-aspartyl-L-phenylalanine methyl ester having a specific surface area of at least 4 m²/g; and
   drying the resulting wet granules to produce dry granules wherein the ratio of I-type crystals of α-aspartyl-L-phenylalanine methyl ester is at least 87%.

2. The process according to claim 1, wherein the drying is conducted at a temperature of lower than 80° C.

3. The process according to claim 1, wherein the drying is conducted under atmospheric pressure.

4. The process according to claim 1, wherein the drying is conducted in a fluidized-bed system.

5. The process according to claim 1, wherein the drying is conducted by air stream drying in a fixed bed system.

* * * * *